United States Patent
Meier et al.

(10) Patent No.: US 6,292,703 B1
(45) Date of Patent: Sep. 18, 2001

(54) NEURAL ELECTRODE ARRANGEMENT

(75) Inventors: Jan H. Meier, Uttenreuth; Erhard Flach; Tobias Breskot, both of Berlin, all of (DE)

(73) Assignee: Biotronik Mess-und Therapiegerate GmbH & Co., Berlin (DE)

( * ) Notice: Subject to any disclaimer, the term of this patent is extended or adjusted under 35 U.S.C. 154(b) by 0 days.

(21) Appl. No.: 09/414,119

(22) Filed: Oct. 8, 1999

(30) Foreign Application Priority Data

Oct. 8, 1998  (DE) .............................................. 198 47 446

(51) Int. Cl.⁷ ...................................................... A61N 1/05
(52) U.S. Cl. ............................................................. 607/118
(58) Field of Search ..................... 607/116–118; 600/373, 600/377, 381

(56) References Cited

U.S. PATENT DOCUMENTS

| | | | |
|---|---|---|---|
| 5,215,089 | 6/1993 | Baker, Jr. ............................... | 128/642 |
| 5,265,608 | 11/1993 | Lee et al. ............................... | 128/642 |
| 5,351,394 | * 10/1994 | Weinberg ............................... | 607/118 |
| 5,487,756 | 1/1996 | Kallesoe et al. ....................... | 607/118 |
| 5,531,778 | 7/1996 | Maschino et al. ..................... | 607/118 |
| 5,689,877 | 11/1997 | Grill, Jr. et al. ........................ | 29/825 |

FOREIGN PATENT DOCUMENTS

| | | |
|---|---|---|
| 196 45 162 | 5/1998 | (DE) . |
| 0 610 301 | 8/1994 | (EP) . |
| 0 865 800 | 9/1998 | (EP) . |
| WO 90/03824 | 4/1990 | (WO) . |
| WO 91/08016 | 6/1991 | (WO) . |
| WO 96/08290 | 3/1996 | (WO) . |

OTHER PUBLICATIONS

G. Naples et al; A Spiral Nerve Cuff Electrode for Peripheral Nerve Stimulation; IEEE Transactions on Biomedical Engineering, vol. 35, No. 11, Nov. 1988, pp. 905–916.

* cited by examiner

Primary Examiner—Jeffrey R. Jastrzab
(74) Attorney, Agent, or Firm—Christie, Parker & Hale, LLP

(57) ABSTRACT

A neural electrode arrangement comprises an elastically deformable carrier body defining a cylindrical internal space therein, and at least one electrode which is fixedly connected to the carrier body and which is in peripherally touchingly operative relationship with the internal space in the carrier body. The electrode is formed from an elongated wire coil.

26 Claims, 4 Drawing Sheets

NEURAL ELECTRODE ARRANGEMENT

FIELD OF THE INVENTION

The invention concerns a neural electrode arrangement.

BACKGROUND OF THE INVENTION

Neural electrodes are used to detect neural activity and excitation signals on a nerve and/or to provide for electrical stimulation of the nerve and must enjoy sound reliable electrical contact with the nerve for the duration of the detection or stimulation period which can extend over months or years without exerting an excessively high pressure on the nerve or even damaging it.

In previous arrangements therefore the actual electrode surfaces are fitted in the form of metal foils to the inside surface of an elastically expandable. spiral or helical main body of plastic material, which after implantation elastically embraces the nerve and in that way provides for a uniform contact pressure with the nerve even in the event of vigorous movements on the part of the patient and even in the event of the nerve swelling. A further development in an arrangement of that kind is to be found for example in WO-A-90/03824.

Besides helical carriers which involve a relatively complicated procedure for fitting them to the nerve and which generally require a special tool for that purpose. carriers of different shapes have also been put forward. Thus US-A-5 487 756 describes a cylindrical elongate sleeve which is divided in the direction of its longitudinal axis and which therefore can be easily opened up and closed again, with a locking bar which is inserted into the sleeve after it has been fitted to the nerve in order securely to close the sleeve around the nerve. In this case the electrodes are formed directly on the carrier by a thin-film process or by galvanisation.

EP-B-O 610 301 describes an arrangement with a carrier of a specific configuration such as to embrace the nerve with two Y-shaped arms of a connecting portion which extends along the nerve The connecting portion and the arms consist of flat silicone material and in this case the electrodes are preferably formed from an iridium foil or band and the carrier body is molded thereon.

In terms of clinical application of arrangements of the above-indicated kinds. it was found that the assembly suffers from unsatisfactory long-term stability.

SUMMARY OF THE INVENTION

An object of the present invention is to provide a neural electrode arrangement which enjoys improved long-term stability.

Another object of the invention is to provide a neural electrode arrangement which is of a simplified structural configuration while ensuring satisfactory and reliable fitting of the neural electrode arrangement to a nerve.

In accordance with the principles of the present invention the foregoing and other objects are attained by a neural electrode arrangement including an elastically deformable carrier body defining a cylindrical internal space therein. and at least one electrode which is fixedly connected to the carrier body and which is peripheral to the cylindrical internal space. The electrode is formed from an elongate wire coil.

As will be apparent from the description hereinafter of a preferred embodiment of the present invention. the invention provides that the electrode or electrodes is or are formed by a structure which is elastically deformable in a plurality of directions. and is or are spatially integrated into the carrier. That serves to at least alleviate or prevent the formation of cracks or ruptures or detachment of the electrode from the carrier, even after use over a relatively prolonged period of time, in conjunction with an elastic carrier. A particularly suitable configuration in that respect is a helical shape which enjoys tensile elasticity in the direction of the longitudinal axis of the coil configuration and which enjoys flexural elasticity and compressive elasticity perpendicularly to the direction of the longitudinal axis.

In accordance with a preferred feature of the invention the at least one electrode is formed from a multiple coil and is flexibly glued into grooves or slots which are specifically pre-formed for same in the carrier body, in such a way that the at least one electrode is disposed at least substantially flush with the inside surface of the carrier body. That substantially eliminates nerve irritation as a consequence of the non-planar electrode surface.

In particular the at least one electrode is glued or cast into the carrier body by means of an elastic materl. more especially a siliconebased casting material or adhesive. By virtue of its own specific elasticity. the electrode is capable of following deformation phenomena or movements of the elastic carrier body without cracks being formed or material detachment phenomena occurring.

In a further preferred feature of the invention the carrier body has a wall which is formed by portions of a hollow cylinder and the thickness of which is at least equal to the diameter of the wire coil. The wall in a technologically advantageous manner has a slot which extends therethrough from the outside surface to the inside surface and into which the coil is inserted. The above-mentioned elastic material for glueing or casting the electrode in place is then introduced into the through slot from the outside surface of the carrier body so that the side of the electrode that faces towards the nerve remains substantially adhesive-free and the electrical properties of the assembly are not adversely affected.

In a further preferred feature of the invention the wire coil is preferably in the form of a double coil comprising two individual metal wires, in order thereby to afford additional safety reserves. The resulting combination of very good electrical properties and a high level of biocompatibility is advantageously achieved by the wire coil being made from platinum and in particular receiving a coating with a fractal surface structure for increasing the effective surface area by at least two orders of magnitude, in a manner which is known per se in relation to pacemaker electrodes.

In accordance with another preferred feature of the invention, with the generally conventional inside diameters of between 2 and 3 mm in respect of the overall arrangement. The wire coil may be of an outside diameter in a range of between 0.2 and 0.6 mm. more especially about 0.45 mm.

In accordance with still another preferred feature of the invention. the at least one electrode is connected to a supply line which is in the form of a stranded wire or a coil and the outside diameter of which is in particular at most equal to the inside diameter of the wire coil constituting the electrode, by means of crimping using a crimping sleeve.

In a preferred configuration of the carrier body it has a central portion and five lateral portions which extend from same substantially perpendicularly and alternately towards both sides and which together with the central portion define the basic shape of a hollow cylinder. A respective electrode is inserted at least into two lateral portions extending towards different sides; preferably, two portions which extend successively towards one side each carry a respective electrode of one polarity. and the portion which is disposed therebetween and which extends towards the other side carries an electrode of the other polarity.

Further objects, features and advantages of the invention will be apparent from the description hereinafter of a preferred embodiment of the invention.

DESCRIPTION OF THE PREFERRED EMBODIMENT

Figure 1:
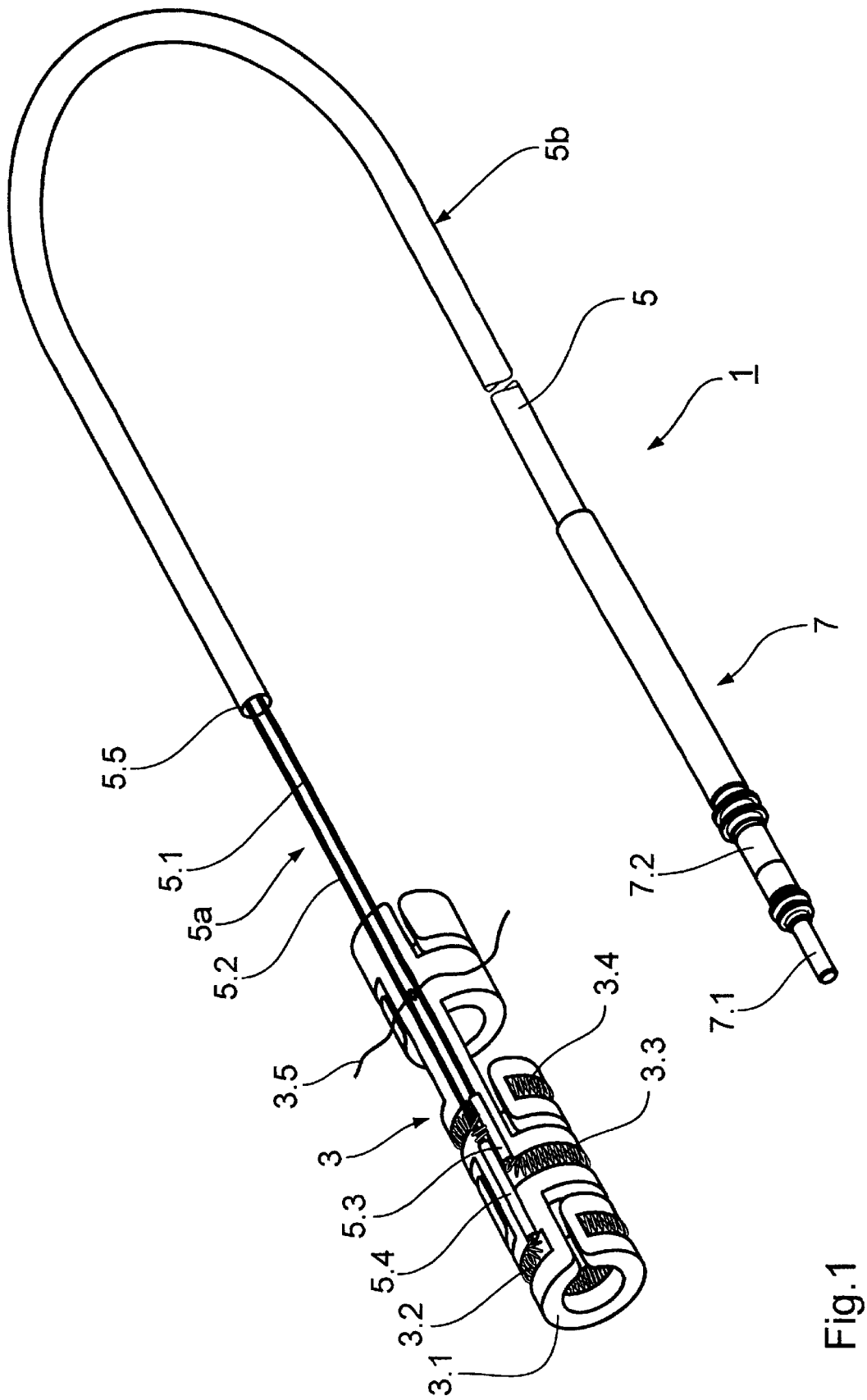
FIG. 1 is a diagrammatic perspective overall view of a preferred embodiment of the invention.

Referring firstly to FIG. 1, shown therein is a perspective overall view of a preferred embodiment of a neural electrode arrangement 1 in accordance with the invention. which besides an actual electrode portion generally indicated at 3, includes a supply line 5 and a plug indicated generally at 7. The electrode portion 3 includes a silicone carrier body 3.1 and first. second and third electrodes indicated at 3.2 through 3.4 together with a glued-on ligature 3.5. The electrode portion 3 will be described in greater detail hereinafter.

The line 5 includes a distal region 5a in which first and second conductor cables 5.1 and 5 2 which at the distal end are connected by means of first and second crimping sleeves 5.3 and 5.4 respectively to the respective electrodes 3.3, 3.2 and 3.4, are exposed without sheathing. and a proximal region 5b in which they fit into a multi-lumen tubular enclosure 5-5. At the proximal end of the line 5 the conductor cables are connected to a pin contact 7.1 and an annular contact 7.2 respectively of the plug 7. Specific details of the plug structure are not identified in FIG.1 and are not described herein as they are known per se and familiar to the man skilled in the art. When using commercially available parts, an adaptor is possibly to be provided for adaptation between the tubular enclosure 5.5 and the plug 7.

Figure 2:
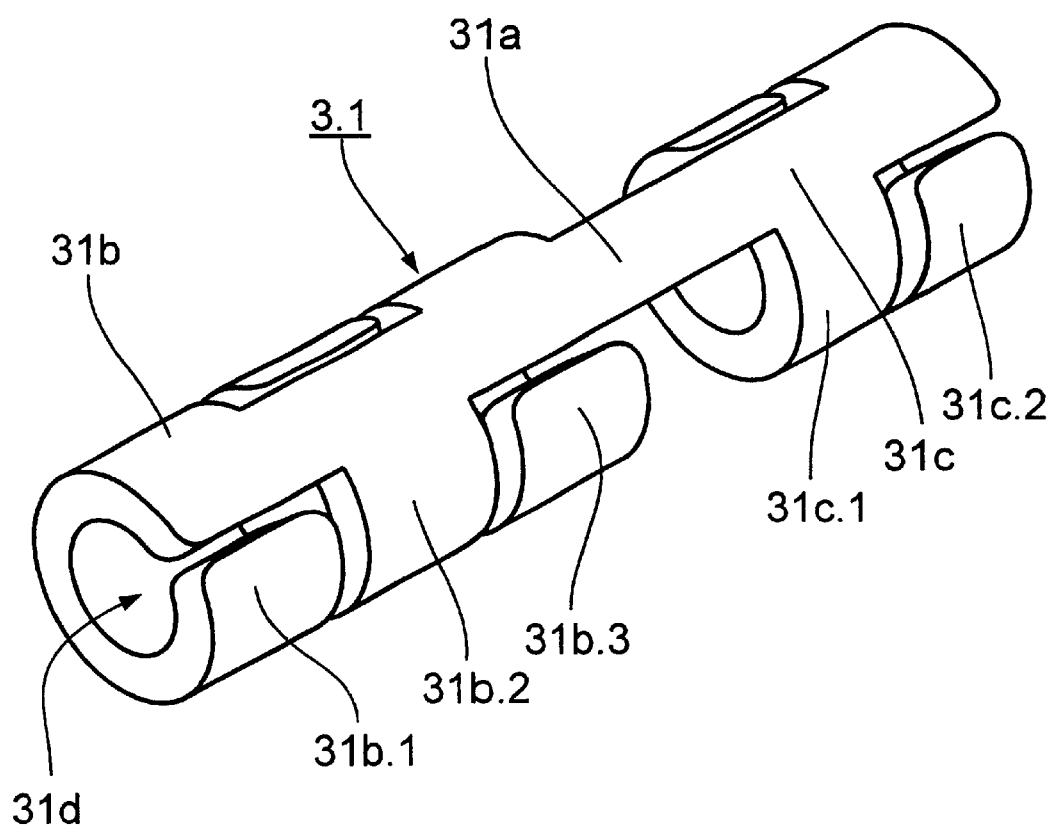
FIG. 2 is a perspective view of the carrier body of the structure shown in FIG.1.
Figure 3:
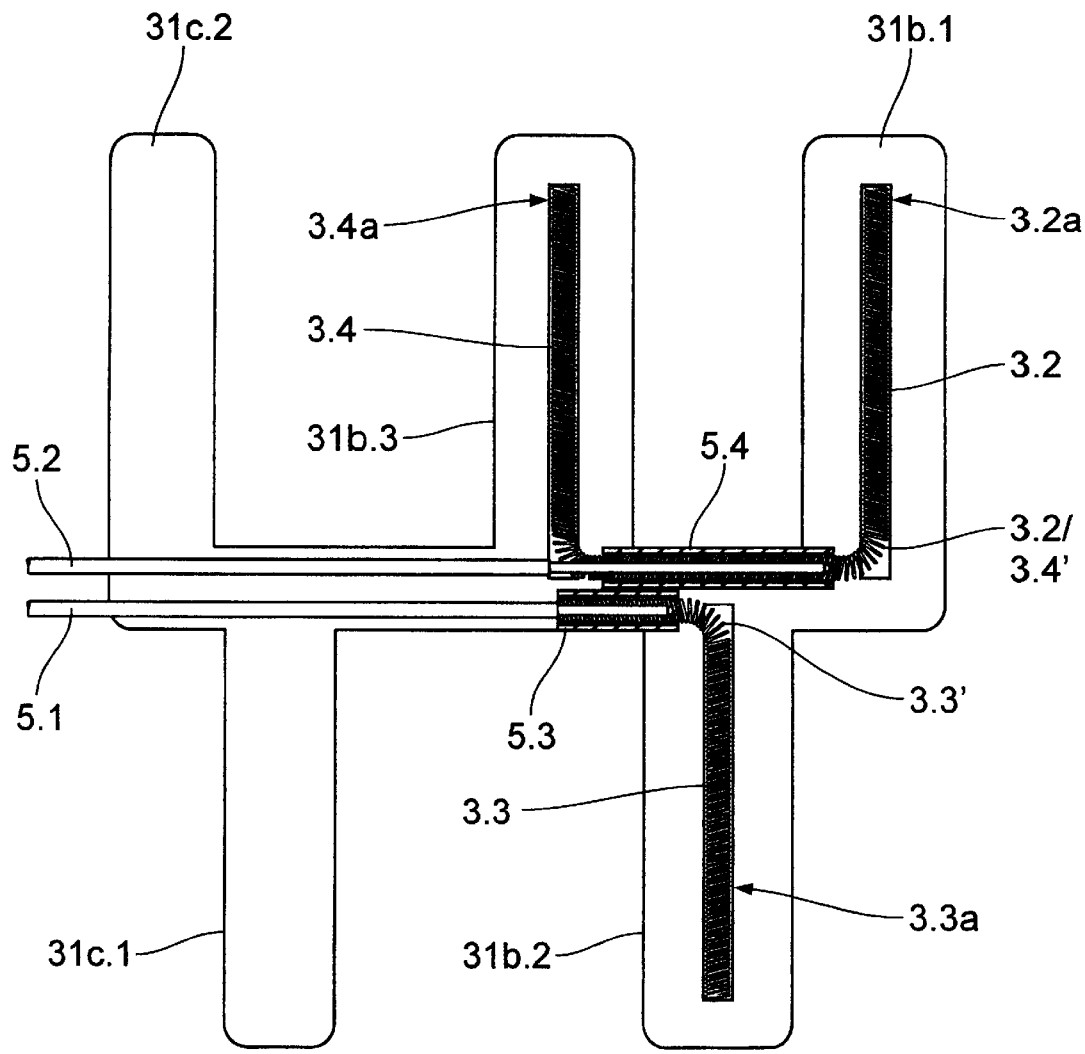
FIG. 3 is a view showing in a developed condition the carrier body of the structure shown in FIG.1, provided with electrodes and supply lines.

Reference will now be made to FIG. 2 which is a diagrammatic perspective view illustrating the configuration of the carrier body 3.1 of the arrangement indicated at 1 in FIG. 3. and also FIG. 3 which is a view in the developed condition into a plane of the carrier body 3-1 which is provided with the electrodes 3.2 through 3.4 and the conductor cables 5.1 and 5.2.

Looking now more specifically at FIG. 2. the carrier body 3.1 which is shown here without slots for the electrodes includes a central portion 31a which connects a distal electrode cuff 31b which accommodates the electrodes 3.2 through 3.4, and a more proximal fixing cuff 31c. The central portion 31a ensures adequate flexural elasticity of the arrangement in the longitudinal and transverse directions thereof. As can be particularly clearly seen now from FIG. 3. in the region of the electrode cuff 31b, three lateral portions 31b.1, 31b.2 and 31b.3 which can also be referred to as cuff wings extend alternately towards both sides from the central portion 31a in perpendicular relationship therewith. while the fixing cuff 31c in turn includes two lateral portions 31c.1 and 31c.2 of a similar nature. All the cuff wings are curved in an annular configuration and as FIG. 2 clearly shows, together define a cylindrical internal space 31d in the electrode portion 3.1. Upon implantation of the neural electrode arrangement. the internal space 31d accommodates a nerve. In terms of its specific dimensioning the carrier body 3.1 is of an overall length of 15 mm while the cuff wings are each of a width of 2 mm and are arranged at spacings of 0.2 mm relative to each other. In this embodiment. the diameter of the cylindrical internal space 31d is 3 mm. The cuff wings or lateral portions 31b.1, 31b.2 and 31b.3 each have slots clearly indicated in FIG. 3 at 3.2a, 3.3a and 3.4a respectively, which extend in the longitudinal direction of each respective cuff wing. for receiving the electrodes.

The insulated conductor cables 5.1 and 5.2 extend lengthwise of the central portion 31a of the carrier body 3.1 to approximately the location of the lateral portion 31b.3, where they are stripped of insulation and pass into the wire coils 3-2/3.4' and 3.3' respectively, which form the electrodes 3.2 and 3.4 on the one hand and 3.3 on the other hand, while also passing into the crimping sleeves 5.4 and 5.3 respectively. together with the electrode wire coils.

Figure 4A:
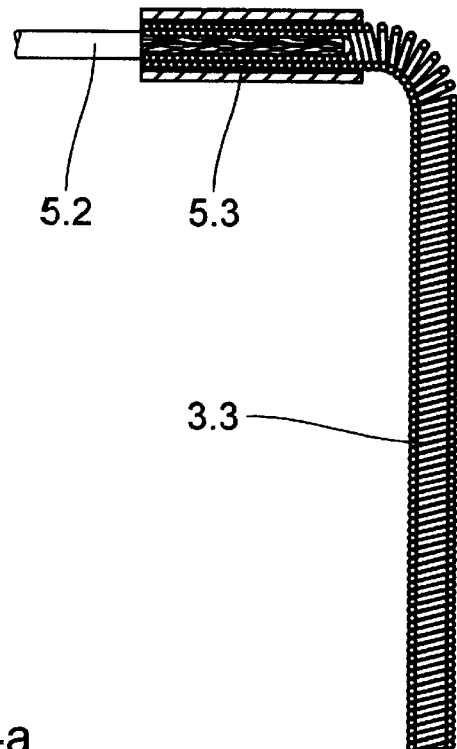
FIGS. 4a and 4b show detail views of the connecting regions between electrodes and supply lines in the FIG.3 arrangement.
Figure 4B:
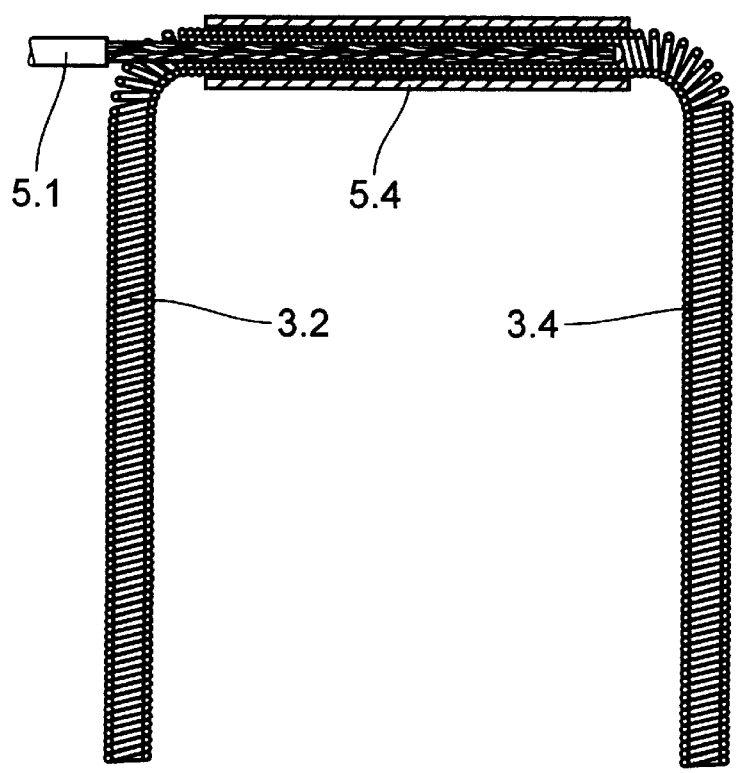

The crimp regions are illustrated on an enlarged scale in FIGS. 4a and 4b respectively. The electrode wire coils are each wound in bifilar mode from a respective pair of platinum wires of a diameter of about 50 $\mu$m, being coated with iridium in a sputtering process to form a fractal surface with an effective surface area which is increased by at least two orders of magnitude. With the size as described herein of the neural electrode arrangement, the electrode wire coils are of a diameter of 0.45 mm and involve lengths of 30 mm as the coil for the electrodes 3.2 and 3-4 and 15 mm as the coil for the electrode 3.3. The conductor cables here are of a diameter of about 0.27 mm and the lengths of the crimp sleeves 5.4 and 5.3 respectively are 2.2 mm and 4.5 mm respectively. After the crimping operation, plastic tubes (not shown) are also drawn for insulation purposes over the fixing regions. For the purposes of inserting the electrodes 3.2 through 3.4 into the appropriately slotted cuff wings 31b.1 through 31b.3 the carrier body is clamped on to a suitable mounting bar and with the cuff wings in the released condition. The electrode wire coils are positioned in the slots and glued from the exterior with silicone adhesive.

It will be appreciated that the above-described embodiment of the present invention has been set forth solely by way of example and illustration of the principles thereof and that various modifications and alterations may be made therein without thereby departing from the spirit and scope of the present invention.

Thus for example the invention also embraces a construction in which one or more electrode wire coils is or are inserted into a carrier body of a spiral or helical configuration.

Moreover, in an embodiment which is modified in comparison with the above-described illustrated specific embodiment. the carrier body may not have slots extending therethrough but may have grooves which open to the inside surface of the carrier body for insertion therein of the electrode wire coils In that case the wall thickness of the carrier body is larger than the diameter of the wire coils.

In a further modified embodiment the electrodes are formed integrally with supply line coils so that the operating procedure of crimping the supply line to the respective wire coil electrodes is no longer required.

Applicant claims priority of German Application No. 198 47 446.6 filed Oct. 8, 1998, a copy of which is enclosed herewith and the content of which is incorporated herein by reference.

What is claimed is:

1. A neural electrode arrangement including
a carrier body a performed at least substantially cylindrical internal space therein and elastically deformable such that a nerve can be inserted into the internal space, and
at least one electrode comprising an elongated wire comprising a plurality of coils fixedly connected to the carrier body nd exposed at an inside surface of the carrier body, wherein th plurality of coils define a longitudinal central axis of the electrode that is not coincident with a longitudinal centrl axis of the carrier body.

2. A neural electrode arrangement as set forth in claim 1 wherein the carrier body has an elongated opening, and wherein the at least one electrode is insered into said elongated opening in substantially flush relationship with the surrounding inside surface of the carrier body.

3. A neural electrode arrangement including
an elastically deformable carrier body having an elongated opening therein, wherein the carrier body defines a preformed at least substantially cylindrical internal space therein, and
at least one electrode comprising an elongated wire comprising a plurality of coils fixedly connected to the carrier body and exposed at an inside surface of the carrier body, wherein the plurality of coils define a longitudinal central axis of the electrode that is not coincident with a longitudinal central axis of the carrier body and wherein the at least one electrode is inserted into said elongated opening in substantially flush relationship with the surrounding inside surface of the carrier body, and
wherein the carrier body has a wall which is formed by portions of a cylinder and the thickness of which is at least equal to the diameter of said wire coil, and
wherein the wall has as said opening a slot extending from the outside surface of the carrier body to the inside surface thereof and in which the at least one electrode is disposed.

4. A neural electrode arrangement as set forth in claim 3 including
an elastic material for securing the at least one electrode in the carrier body by a glueing action, the elastic material being introduced into said slot from the outside surface of the carrier body.

5. A neural electrode arrangement as set forth in claim 3 including
an elastic material for securing the at least one electrode in the carrier body by a casting action, the elastic material being introduced into said slot from the outside surface of the carrier body.

6. A neural electrode arrangement as set forth in claim 1 including
an elastic material securing the at least one electrode in the carrier body by a glueing action.

7. A neural electrode arrangement as set forth in claim 6 wherein said elastic material is a silicone-based material.

8. A neural electrode arrangement as set forth in claim 1 including
an elastic material securing the at least one electrode in the carrier body by a casting action.

9. A neural electrode arrangement as set forth in claim 8 wherein said elastic material is a silicone-based material.

10. A neural electrode arrangement as set forth in claim 1 wherein the wire coil is in the form of a double coil comprising first and second individual metal wires.

11. A neural electrode arrangement as set forth in claim 1 wherein the wire coil comprises platinum.

12. A neural electrode arrangement as set forth in claim 11 and further including
a coating disposed on the at least one electrode with a fractal surface structure for increasing the effective surface area of the at least one electrode by at least two orders of magnitude.

13. A neural electrode arrangement as set forth in claim 11 and further including
a sputtered transition metal coating disposed on the at least one electrode with a fractal surface structure for increasing the effective surface area of the at least one electrode by at least two orders of magnitude.

14. A neural electrode arrangement as set forth in claim 1 wherein the wire coil comprises a platinum alloy.

15. A neural electrode arrangement as set forth in claim 14 and further including
a coating disposed on the at least one electrode with a fractal surface structure for increasing the effective surface area of the at least one electrode by at least two orders of magnitude.

16. A neural electrode arrangement as set forth in claim 14 and further including
a sputtered transition metal coating disposed on the at least one electrode with a fractal surface structure for increasing the effective surface area of the at least one electrode by at least two orders of magnitude.

17. A neural electrode arrangement as set forth in claim 1 wherein the wire coil is of an outside diameter in a range of between 0.2 and 0.6 mm.

18. A neural electrode arrangement as set forth in claim 17 wherein the wire coil is of an outside diameter of about 0.45 mm.

19. A neural electrode arrangement as set forth in claim 1 and further including
a line means for electrically connecting said at least one electrode to a source of power, and
means of crimping said line means to said at least one electrode.

20. A neural electrode arrangement as set forth in claim 19 wherein said line means is in the form of a stranded wire.

21. A neural electrode arrangement as set forth in claim 19 wherein said line means is in the form of a coiled wire.

22. A neural electrode arrangement as set forth in claim 19 wherein said line means is of an outside diameter which is at most equal to the inside diameter of the electrode wire coil.

23. A neural electrode arrangement including
an elastically deformable carrier body defining an at least substantially cylindrical internal space therein, and
at least one electrode comprising an elongated wire coil fixedly connected to the carrier body and exposed at an inside surface of the carrier body,
wherein said carrier body is of an elongated configuration and comprises a central portion extending in the longitudinal direction of the carrier body and first, second, third, forth and fifth lateral portions which extend from said central portion alternately towards first and second sides thereof in substantially perpendicular relationship with said central portion, said lateral portions and said central portion defining the basic shape of a hollow cylinder, and wherein a respective electrode is disposed at least in first and second lateral portions extending towards different sides of said central portion.

24. A neural electrode arrangement including a carrier body defining a preformed at least substantially cylindrical internal space therein and elastically deformable such that a nerve can be inserted into the internal space, at least one electrode comprising an elongated wire comprising a plurality of coils, wherein; the plurality of coils define a longitudinal central axis of the electrode that is not coincident with a longitudinal central axis of the carrier body, and means connecting the at least one electrode to the carrier body in circumscribingly operative relationship with said internal space in the carrier body.

25. A neural electrode arrangement including an elastically deformable carrier body having an elongated opening therein, wherein the carrier body defines a preformed at least substantially cylindrical internal space therein, and at least one electrode comprising an elongated wire comprising a plurality of coils fixedly connected to the carrier body and exposed at an inside surface of the carrier body, wherein the plurality of coils define a longitudinal central axis of the electrode that is not coincident with a longitudinal central axis of the carrier body and wherein the at least one electrode is inserted into said elongated opening in substantially flush relationship with the surrounding inside surface of the carrier body.

26. A neural electrode arrangement including an elastically deformable carrier body having a preformed at least substantially cylindrical internal space therein, and at least one electrode comprising an elongated wire comprising a plurality of coils fixedly connected to the carrier body and exposed at an inside surface of the carrier body, wherein the plurality of coils define a longitudinal axis located toward the opposite side of the carrier body from the inside surface.

* * * * *